United States Patent
Wagner, Jr.

(10) Patent No.: US 7,244,562 B2
(45) Date of Patent: Jul. 17, 2007

(54) RECA ASSISTED DETECTION OF MUTATIONS, SINGLE NUCLEOTIDE POLYMORPHISMS AND SPECIFIC SEQUENCES

(75) Inventor: Robert E. Wagner, Jr., Carr, CO (US)

(73) Assignee: Gene Check, Inc., Ft. Collins, CO (US)

( * ) Notice: Subject to any disclaimer, the term of this patent is extended or adjusted under 35 U.S.C. 154(b) by 298 days.

(21) Appl. No.: 10/283,243

(22) Filed: Oct. 30, 2002

(65) Prior Publication Data

US 2003/0108936 A1 Jun. 12, 2003

(51) Int. Cl.
*C07H 21/04* (2006.01)
*C12P 19/34* (2006.01)
*C12Q 1/68* (2006.01)

(52) U.S. Cl. .................. 435/6; 435/91.1; 536/23.1; 536/24.3

(58) Field of Classification Search .................. 435/6, 435/91.1, 91.2; 536/23.1, 24.1
See application file for complete search history.

(56) References Cited

U.S. PATENT DOCUMENTS

| 5,273,881 A | | 12/1993 | Sena et al. |
| 5,670,316 A | * | 9/1997 | Sena et al. ................. 435/6 |
| 5,679,524 A | * | 10/1997 | Nikiforov et al. ............ 435/6 |
| 6,013,431 A | | 1/2000 | Soederlund et al. |

| 2003/0180746 A1 | * | 9/2003 | Kmiec et al. .................. 435/6 |

OTHER PUBLICATIONS

Rigas et al. "Rapid plasmid library screening using RecA-coated biotinylated probes" PNAS, vol. 83, Dec. 1986, pp. 9591-9595.*

* cited by examiner

*Primary Examiner*—Carla J. Myers
*Assistant Examiner*—Sarae Bausch
(74) *Attorney, Agent, or Firm*—Jennifer M. McCallum, Esq.; The McCallum Law Firm, P.C.

(57) ABSTRACT

A method for detecting a specific sequence, a mutation and/or a polymorphisms, including a single nucleotide polymorphism (SNP), is based on the use of RecA-like recombinase protein and primer extension (PE) or oligonucleotide ligation assays (OLA). RecA coated, specific DNA oligonucleotide probes (RecA filaments) are used for homology searching in duplex DNA. Location of homologous sequences results in the formation of D-loop or double D-loop structures containing a duplex regions comprising the oligonucleotide probe and one strand of the target DNA. In the case of the PE methods, probes are selected to terminate with their 3' end adjacent to the site of mutation or SNP such that a single nucleotide or terminator addition to the primer will be diagnostic of the mutation or SNP. In the case of the OLA methods, sets of oligonucleotide probes (ligation partners) are selected to have adjacent ends terminate at, or adjacent to, the site of mutation or SNP such that ligation is possible only when both ends are correctly base-paired. Successful ligation is diagnostic of the specific sequence, mutation or SNP. Also disclosed are compositions and kits useful for practicing the foregoing methods.

11 Claims, 3 Drawing Sheets

RECA ASSISTED DETECTION OF MUTATIONS, SINGLE NUCLEOTIDE POLYMORPHISMS AND SPECIFIC SEQUENCES

BACKGROUND OF THE INVENTION

1. Field of the Invention

The present invention in the fields of molecular biology and medicine relates to methods for detecting specific sequences in double-stranded DNA samples and for detecting mutations and polymorphisms involving as little as one base change (Single Nucleotide Polymorphism—SNP) or additions to or deletions from the wild-type DNA sequence.

2. Description of the Background Art

Progress in human molecular and medical genetics depends on the efficient and accurate detection of mutations and sequence polymorphisms, the vast majority of which results from single base substitutions (as in SNPs) and small additions or deletions. Assays capable of detecting the presence of a particular mutation, SNP or mutant nucleic acid sequence in a sample are therefore of substantial importance in the prediction and diagnosis of disease, forensic medicine, epidemiology and public health. Such assays can be used, for example, to detect the presence of a mutant gene in an individual, allowing determination of the probability that the individual will suffer from a genetic disease and to detect the presence of an infectious agent in a patient. The ability to detect a mutation has taken on increasing importance in early detection of cancer or discovery of susceptibility to cancer with the discovery that discrete mutations in cellular oncogenes can result in activation of that oncogene leading to the transformation of that cell into a cancer cell and that mutations inactivating tumor suppressor genes are required steps in the process of tumorigenesis The detection of SNPs has assumed increased importance in the identification and localization (mapping) of genes, including those associated with human and animal diseases. Further, the continuing and dramatic increase in the number of SNPs of known location in the genome will allow genome wide scanning for identification of disease associated genes.

To realize the maximum potential benefits of this explosion of genetic information, both in research and in health care applications, and to increase the utility and applicability of mutation and SNP detection, will require improvements in current technologies, including increases in assay sensitivity and multiplexing ability and reductions in assay complexity and cost. The present invention is directed to methods of specific sequence, SNP and mutation detection embodying such improvements.

Most methods devised to attempt to detect genetic alterations comprising one or a few bases involve amplification of specific DNA regions by polymerase chain reaction (PCR). However, PCR amplification has severe limitations with respect to its utility in mutation and SNP detection:

1. PCR amplification is a relatively low fidelity process. Misincorporation during amplification is a particular problem in those detection methods that involve denaturation and annealing of PCR amplicons to form mutant: wild type heteroduplexes in which mutations and SNPs are revealed as mismatched or unpaired bases. Given the random nature of PCR errors, virtually all will be in such mismatches following annealing and will contribute to background signal. In gel based applications these error-containing molecules will generally not interfere. However, in high through put applications involving mismatch binding or mismatch cleaving, high background signals can greatly limit the utility of a method and frequently require that PCR fragments be kept relatively short.

2. PCR is subject to mispriming. Mispriming involves primer extension at non-target sites, which can occur even when only a relatively short portion of the 3' end of a primer is transiently paired with some sequence in the target DNA. Mispriming can produce long single-stranded fragments which can adopt mismatch-containing secondary structure. Mispriming is also a major problem in those methods which utilize primer extension for SNP detection. These methods use oligonucleotides which are complementary to a region of target DNA immediately adjacent to the SNP or mutation to be genotyped such that the first nucleotide added by DNA polymerase to the 3' end of the oligonucleotide will be complementary to and diagnostic for the SNP. Generally, these methods use specific nucleotide terminators (e.g., dideoxy or acyclo nucleotides) which are detectably labeled. Mispriming is such a problem with these methods that they generally require pre-amplification of the target region.

3. Some DNA regions are refractory to amplification. Because PCR requires denaturation of the target DNA, it provides the opportunity for the target DNA to adopt secondary structures, some of which may prevent primer annealing or extension.

4. PCR multiplexing potential is limited. The intricacies of primer design and the variability of PCR conditions depending on target and primer sequences coupled with the potential for interference between primer sets makes it unlikely that PCR will ever attain multiplexing levels as high as 100 fold, levels generally considered as the minimum desirable level for high through put SNP and mutation detection applications.

Therefore, a method of mutation/SNP that is not dependent on PCR amplification would have immediate and widespread utility both in research and health care. The present invention does not require PCR amplification.

Oligonucleotide Extension Assays

Oligonucleotide or primer extension (PE) assays allow detection of SNPs and mutations by addition of allele-specific nucleotides or nucleotide analogs to oligonucleotides, the 3' end of which terminate at the nucleotide adjacent to the site in question. PE assays (Goelet, P et al., U.S. Pat. Nos. 5,888,819 and 6,004,744) are powerful methods for detecting known mutations and SNPs. PE requires PCR amplification of target DNA, removal of deoxynucleotide triphosphates (dNTPs) and PCR primers and addition of a third primer adjacent to the mutation or SNP site. Polymerase is then allowed to extend the specific primer by a single base by adding the nucleotide complementary to the mutation or SNP. Labeled terminator nucleotide analogs, e.g., dideoxy, arabinoside or acyclo nucleotides, are most commonly used. The precise nature of the nucleotide added is diagnostic of the allele in the target DNA. By using multiple differently labeled terminating nucleotide analogs, it is possible to genotype a given SNP or mutation site completely in a single reaction. Extension primers can contain 5' adducts, such as biotin or specific oligonucleotide tails to allow immobilization and subsequent detection of the primers labeled by extension. Clearly, extension primers can be designed to allow detection of virtually all SNPs as well as deletion and addition mutations.

Primer extension assays suffer from the requirement for PCR amplification (due to problems with mispriming if extension primers are used with genomic DNA) and the consequent need to design three primers for each SNP or mutation site. Heretofore, and in clear distinction to the present invention, use of primer extension assays without target DNA denaturation and amplification have not been possible.

Oligonucleotide Ligation Assays (OLA)

The OLA method of SNP detection (Landegren, U et al., U.S. Pat. No. 4,988,617, *Science* 241:1077-1080 (1988), Methods ?? 9:84-90 (1996); Nickerson, D A et al., *Proc Natl Acad Sci* 87:8923-8927 (1990)) utilizes two oligonucleotide probes which are complementary to the target DNA flanking the SNP/mutation site. One oligonucleotide ends at the SNP site and the other ends at the nucleotide adjacent to the SNP site such that, when annealed to target DNA, the ends of both oligonucleotides are base-paired at the site of the SNP and can be joined (ligated) by DNA ligase. If there is a mismatch at the joint, i.e., if the end base in the oligonucleotide that covers the SNP/mutation is not complementary to the SNP/mutation, ligation cannot occur. Ligated products can be detected on gels without labeling by virtue of their increased length relative to the oligonucleotide probes.

To avoid the use of gels, OLA has been performed with probes which allow ligation product immobilization (Nickerson, D A et al., *Proc Natl Acad Sci* 87:8923-8927 (1990)). For example, one oligonucleotide probe can be prepared with a 5' biotin adduct to allow immobilization to avidin- or streptavidin-coated plates or microspheres. This probe generally ends one nucleotide 5' of the SNP. The other probe is detectably labeled, either internally or at the 3' end. Detectable labels include fluorescent, radioactive and antigenic labels such as digoxigenin. In this example, the 5' nucleotide of the detectably labeled probe would be complementary to one allele of the SNP or mutation. Target DNA must be denatured and the ligation oligonucleotides allowed to anneal. If the allele in question is present in the target DNA, ligation will occur and the labeled oligonucleotide will be linked to the biotinylated oligonucleotide such that label can be bound to avidin/streptavidin coated plates or microspheres. By combining two differently labeled oligonucleotides, each with their 5' nucleotide complementary to a different allele of the SNP or mutation, it is possible to perform complete genotyping in a single assay (Samiotaki et al., *Genomics* 20:238-242 (1993)).

OLAs have also been used to detect changes in mononucleotide repeat sequence lengths (Zirvi, et al., *Nucl Acids Res* 27:e40 (1999)). The system is able to discriminate repeat sequences that vary by one nucleotide in sequences of up to 16 mononucleotide repeats. Notably, the above authors stated that: "The greatest source of error for analysis of mononucleotide repeat sequences, however, is the error generated during PCR amplification of microsatellite repeats."

OLA has been used with flow cytometry and limited multiplexing (Iannone, et al., *Cytometry* 39:131-140 (2000)). In this system, ligation products were immobilized to microspheres (Luminex) by means of a 25 base specific oligonucleotide "tail". Target DNA was PCR-amplified prior to ligation. Simultaneous genotyping of 9 SNPs was demonstrated.

By virtue of their precision and specificity OLAs have enjoyed widespread application in mutation and SNP detection. However, and in clear distinction to the present invention, OLAs absolutely require denaturation of target DNA and have not been successful without amplification of target sequences.

RecA

RecA is a bacterial protein involved in DNA repair and genetic recombination and has been best characterized in *E. coli*. RecA is the key player in the process of genetic recombination, in particular in the search and recognition of sequence homology and the initial strand exchange process. RecA can catalyze strand exchange in the-test tube. Recombination is initiated when multiple RecA molecules coat a stretch of single-stranded DNA (ssDNA) to form what is known as a RecA filament. This filament, in the presence of ATP, searches for homologous sequences in double-stranded DNA (dsDNA). When homology is located, a three stranded (D-loop) structure is formed wherein the RecA filament DNA is paired with the complementary strand of the duplex.

RecA homology searching is extremely precise and RecA has been used to facilitate screening of plasmid libraries for plasmids containing specific sequences (Rigas et al., *Proc Natl Acad Sci* USA. 83:9591-9595 (1986)). In this approach, biotinylated ssDNA probes are reacted with RecA to form RecA filaments. The filaments are used for homology searching in circular plasmid DNA. When the probes are removed by binding to avidin, those plasmids containing sequences homologous to the probes are isolated by virtue of the triple stranded (D-loop) structures formed by the RecA filament and the plasmid duplex. Stabilization of these structures requires the use of adenosine 5'-[γ-thio]triphosphate (ATP[γ-S]) in place of ATP. ATP[γ-S] allows homology searching by RecA, but is non-hydrolyzable and thus does not allow RecA to dissociate from the triple stranded structure.

RecA has also been used, in a variety of applications, to facilitate the mapping and/or isolation of specific DNA regions from bacterial and human genomic DNA (Ferrin, L J, et al., *Science* 254:1494-1497 (1991); Ferrin, L J, et al., *Nature Genetics* 6:379-383 (1994); Ferrin, L J et al., *Proc Natl Acad Sci* 95:2152-2157 (1998), Sena et al., U.S. Pat. Nos. 5,273,881 and 5,670,316; Sena and Zarling, *Nature Genetics* 3:365-371 (1993)). In one of these applications (Ferrin et al., 1991, supra; 1994, supra; U.S. Pat. No. 5,707,811), RecA is used in conjunction with restriction enzymes (sequence-specific double strand DNA endonucleases) to allow isolation or identification of specific DNA fragments. RecA filaments are prepared and reacted with genomic DNA under conditions that allow triple strand (D-loop) structure formation. The DNA is then treated with either a restriction endonuclease or a modification methylase (methylase action transfers a methyl group to the specific recognition sequence of a specific restriction endonuclease, thus protecting the sequence from endonuclease digestion). The presence of the RecA filament in the triple strand structure prevents digestion or methylation.

In a more recently developed application (Ferrin et al., 1998, supra and U.S. Pat. No. 5,707,811;), specific RecA filaments were used to protect restriction endonuclease generated "sticky ends" from being filled in by DNA polymerase such that, upon removal of the RecA filaments, specific fragments can be cloned into plasmid vectors. In this application (??), genomic DNA is digested with one or more restriction enzymes that produce recessed 3' ends. A specific fragment from this digestion is protected by triple strand structure formation with a pair of RecA filaments. The recessed 3' ends of the remaining fragments are then filled in with a polymerase. The polymerase is removed or inactivated, the RecA, filament is removed and the specific fragment cloned by virtue of its sticky ends.

RecA has been used in association with DNA ligase to label specific DNA fragments (Fujiwara, J et al., *Nucl Acids*

*Res* 26:5728-5733 (1998)). Oligonucleotides are designed to allow the 3' end to form a double-stranded region by folding back on a portion of itself (hairpin), RecA is then used to coat the remaining single-stranded 3' region and the resulting RecA filament used to perform homology searching. When a terminus of the target DNA is complementary to the single-stranded portion of the oligonucleotide, ligation can covalently link the oligonucleotide, which can be labeled at the 5' end with a detectable label, to the target DNA to allow detection or isolation of specific target DNA sequences without denaturation of the target DNA.

Formation of RecA catalyzed double D-loops has been used to identify and isolate specific DNA regions from ds DNA (Sena et al., supra; Sena and Zarling, supra). This method requires relatively long DNA probes (>78 nucleotides), and complementarity between the probes and double D-loops in order to provide for a stable structure. The above documents note the possibility of introducing a detectable label into the probe by oligonucleotide extension with DNA polymerase. Importantly, this method is suited only for detection of specific sequences in a target DNA but is of no use in detecting mutations or SNPs—both of which are objectives of the present invention.

In summary, no applications of RecA have heretofore been proposed that allow the detection of mutations or SNPs or the identification of sequences which differ from a wild type sequences by only one or a few nucleotides.

All statements as to the date or representation as to the contents of documents cited herein is based on the information available to the applicant and does not constitute any admission as to the correctness of the dates or contents of these documents.

SUMMARY OF THE INVENTION

The present invention is directed to RecA assisted methods for detecting a mutation and/or a SNP or a specific DNA sequence in a double-stranded target or test DNA molecule. The general methods are referred to as RecA/Primer extension (RecA/PE) and RecA/Oligonucleotide ligation assay (RecA/OLA).

The RecA/PE method of SNP and mutation detection comprises the following steps:

(a) providing a ss DNA oligonucleotide probe having a known nucleotide sequence complementary to (at least a part of) the sequence of the target DNA, which probe is optionally detectably labeled or contains an adduct positioned internally or at the probe's 5' end, which adduct allows immobilization. The sequence of the probe is such that, when annealed to the complementary region of the target DNA, the probe's 3' end is adjacent to the site of a mutation or SNP;

(b) contacting the probe with a RecA protein or a homologue thereof, defined in more detail below, to form a RecA filament;

(c) contacting the RecA filament with target dsDNA, thereby allowing RecA filament homology searching and formation of a three stranded DNA D-loop structure in the target DNA. The D-loop structure comprises the probe and the two strands of the target DNA;

(d) contacting the DNA D-loop structure, in the presence of a DNA polymerase capable of primer extension, with one or more detectably labeled dNTP or, preferably, with one or more detectably labeled terminators of primer dependent extension, wherein if more than one dNTP or terminator is employed, only one dNTP or terminator is detectably labeled. In a preferred embodiment, a different and distinguishable label is used for each dNTP or each terminator; and (e) detecting the presence of the dNTP or terminator covalently bonded to the 3' end of the oligonucleotide probe, wherein, if a single dNTP or terminator is employed, the presence of the dNTP or terminator the is indicative of the presence of the specific mutation or the SNP in the target DNA. If multiple dNTPs or terminators are employed, the identity of the attached dNTP or terminator is indicative or the presence of a specific allele of the SNP or mutation sequence.

The RecA/OLA method of SNP and mutation detection comprises the following steps:

(a) providing two or more ssDNA oligonucleotide probes (a first and a second oligonucleotide) having known nucleotide sequences complementary to the sequence of (at least a part of) the target or test DNA, which probles are optionally detectably labeled or contain an adduct to allow immobilization. The sequence of the probes is such that, when annealed to the complementary region of the target DNA, the probes are contiguous and their adjacent ends include, bracket or overlap the site of a mutation or SNP such that the ends may be covalently linked by a DNA ligase unless (1) there is a base pair mismatch between the end of one or both probes and the target DNA or (2) the ends overlap because of a deletion in the target DNA or (3) there is a gap between the probes because of the addition of nucleotide(s) in the target DNA;

(b) contacting the probes with a RecA protein or a homologue thereof to form RecA filaments;

(c) contacting the RecA filaments with target dsDNA, thereby allowing homology searching by the RecA filaments and formation of (1) a three stranded DNA D-loop structure in the target DNA, which D-loop structure comprises two oligonucleotides complementary to one of the strands of the target DNA and the two strands of the target DNA, or (2) a four stranded double D-loop structure in the target DNA, which double D-loop structure comprises four oligonucleotides, two complementary to each strand of the target DNA, and the two strands of the target DNA;

(d) contacting the D-loop or double D-loop structure with a DNA ligase under conditions that permit covalent bonding of directly adjacent ends of the oligonucleotides (provided that there is no base pair mismatch between the end of either adjacent oligonucleotide and the target DNA) to form linked oligonucleotide probe molecules; and (e) detecting the linked oligonucleotide probe molecules, the presence of which is indicative of the mutation or SNP sequence or allele in the target DNA.

Also provided are methods for detecting specific sequences in a sample of ds target or test DNA, for example, detecting the DNA of an infectious viral or bacterial agent in a sample of mammalian genomic DNA, wherein D-loop or double D-loop formation and consequent primer extension or oligonucleotide ligation are dependent upon the presence in the target DNA sample of the specific sequence.

The RecA/PE method of specific sequence detection comprises:

(a) providing a ss olignucleotide probe having a known nucleotide sequence complementary to the specific DNA sequence, which probe is optionally detectably labeled or contains an adduct positioned internally or at the probe's 5' end, to allow immobilization;

(b) contacting the probe with a RecA protein or a homologue thereof to form a RecA filament;

(c) contacting the RecA filament with target dsDNA, wherein RecA filament homology searching and the presence in the target DNA sample of sequence complementary to the probe DNA sequence allows formation of a three stranded DNA D-loop structure in the target DNA, which D-loop structure comprises the probe and the two strands of the target DNA;

(d) contacting the DNA D-loop structure, in the presence of a DNA polymerase capable of primer extension, with one or more detectably labeled dNTPs or, preferably, with one or more detectably labeled terminators of primer dependent extension; and (e) detecting the presence of the dNTP or terminator covalently bound to the 3' end of the DNA probe, wherein the presence of the dNTP or the terminator is indicative of the presence of the specific DNA sequence in the target DNA sample.

The RecA/OLA method of specific sequence detection comprises:

(a) providing two or more ss DNA probes (a first and a second olignucleotide probe) having known nucleotide sequences complementary to a specific DNA sequence, which probles are optionally detectably labeled or contain an adduct to allow immobilization. The sequence of which probes is such that, when annealed to the specific DNA sequence, the probes are contiguous and their adjacent ends may be covalently linked by a DNA ligase;

(b) contacting the probes with a RecA protein or a homologue thereof to form RecA filaments;

(c) contacting the RecA filaments with target dsDNA, wherein RecA filament homology searching and the presence in the target DNA sample of sequence complementary to the probe DNA sequence allows formation of (1) a three stranded DNA D-loop structure in the target DNA, which D-loop structure comprises two probes complementary to one of the strands of the target DNA and the two strands of the target DNA, or (2) a four stranded double D-loop structure in the target DNA, which double D-loop structure comprises four probes, two complementary to each strand of the target DNA, and the two strands of the target DNA;

(d) contacting the D-loop or double D-loop structure with a DNA ligase under conditions that permit direct covalent bonding of adjacent ends of the probes to form linked probe molecules;

(e) detecting the linked probe molecules, the presence of which is indicative of the specific sequence or allele in the target DNA.

The RecA protein is preferably from *E. coli*.

In the methods described herein, the labels may be any suitable detectable label, e.g., a fluorophore, a chromophore, a radionuclide, biotin, digoxigenin, etc. The probe DNAs, dNTPs or terminators may be directly labeled by direct bonding or binding of the label. However, the term "detectably labeled," includes "indirect" labeling wherein the "detectable label" is a primary antibody, or any other binding partner, which is directly labeled. Alternatively, the detectable label may be a combination of an unlabeled primary antibody with a directly labeled secondary antibody specific for the primary antibody.

In the present method, probe DNA may be in solution or immobilized to any solid support and may be immobilized either before or after reaction with RecA and target DNA.

In the above methods, the single DNA D-loop structure may be further stabilized by the addition, before step (d) above of the single strand DNA binding (SSB) protein (Chase et al., *Nucl Acids Res* 8:3215-3227 (1980)), or an SSB homologue.

In the above methods of SNP and mutation detection, stability of the three strand structure can also be enhanced by utilizing a DNA oligonucleotide complementary to the opposite strand of the target DNA to which the probe or probes are complementary. In this case, the oligonucleotide should contain a nucleotide at the site of the mutation or SNP which is not complementary to any allele of the mutation or SNP.

The present invention also provides a kit useful for practicing any of the above methods, the kit being adapted to receive therein one or more containers, the kit comprising:

(a) a first container containing RecA protein;

(b) a second container containing ss DNA probes; and (c) a third container or plurality of containers containing buffers and reagent or reagents including one or more labeled dNTPs or terminator nucleotide analogs and a DNA polymerase capable of extending DNA probes when the probes are annealed to target DNA.

In another embodiment, the kit comprises:

(a) a first container containing RecA filaments, the filaments comprising RecA protein, or a homologue thereof, and ssDNA probes;

(b) a second container or plurality of containers containing buffers and reagent or reagents including one or more labeled dNTPs or terminating nucleotide analogs and a DNA polymerase capable of extending the probes when the probes are annealed to target DNA.

In another embodiment, the kit is adapted to receive therein one or more containers, the kit comprising:

(a) a first container containing RecA protein;

(b) a second container containing ssDNA probes, which may optionally be detectably labeled or contain adducts to allow immobilization;

(c) a third container or plurality of containers containing buffers and reagent or reagents including a DNA ligase capable of linking DNA probes when the probes are annealed to target DNA without a base pair mismatch at their adjacent ends.

The kit may also comprise:

(a) a first container containing RecA filaments, the filaments comprising RecA protein, or a homologue thereof, and ss DNA probes, which may optionally be detectably labeled or contain adducts to allow immobilization;

(b) a second container or plurality of containers containing buffers and reagent or reagents including a DNA ligase capable of linking DNA probes when the probes are annealed to target DNA without a base pair mismatch at their adjacent ends.

BRIEF DESCRIPTION OF THE DRAWINGS

FIG. 1 shows the RecA/PE (Primer Extension) method. An oligonucleotide "probe" is mixed with RecA protein. RecA coats the probe to form a "RecA filament." RecA filament is added to target DNA and allowed to perform homology searching and to form a triple stranded or "D-loop" structure. A DNA polymerase is added along with labeled nucleotide triphosphates or nucleotide analog terminators. The terminator or triphosphate complementary to the SNP allele or to the first base of a larger mutation will be added to the oligonucleotide probe. Cycling involves displacement of the original oligonucleotide probe, either before or because of a second round of homology searching by a RecA filament.

FIG. 2 shows the RecA/OLA (Oligonucleotide Ligation Assay) single D-loop method. Oligonucleotide probes are mixed with RecA protein. RecA coats the probes to form RecA filaments. The RecA filaments are added to target DNA and allowed to perform homology searching and to form a triple stranded or "D-loop" structure (Step A). If the oligonucleotide probes are perfectly based paired at their adjoining ends, DNA ligase is able to covalently link them (Step B). Release of ligated fragment (Step C) regenerates intact target DNA and allows the process (Steps A-C) to repeat (Cycling). Note that the release of the ligated fragment may occur before or as a result of homology searching.

FIG. 3 shows the RecA/OLA (Oligonucleotide Ligation Assay) double D-loop method. Oligonucleotide probes are mixed with RecA protein. RecA coats the probes to form RecA filaments. The RecA filaments are added to target DNA and allowed to perform homology searching and to form a four stranded or "double D-loop" structure. If the oligonucleotide probes are perfectly based paired at their adjoining ends, DNA ligase is able to covalently link them. Release of ligated fragment regenerates intact target DNA and allows the process to repeat (Cycling). The stability of the double D-loop structure will normally require further homology searching to release the ligated fragments, which will allow exponential signal amplification.

DESCRIPTION OF THE PREFERRED EMBODIMENTS

The present inventor has devised a novel technology for detecting mutations or SNPs or for detecting specific sequences in ds DNA samples, all based on RecA mediated homology searching followed by genotype- or sequence-specific primer extension (RecA/PE) or genotype- or sequence-specific oligonucleotide ligation (RecA/OLA). In general, the present methods employ:

(1) a ds target or test DNA molecule, which may be any synthetic, viral, plasmid, prokaryotic or eukaryotic DNA from any source, including, but not limited to, genomic DNA, restriction digestion fragments or DNA amplified by PCR or by any other means;

(2) ss DNA probes, which might be any synthetic oligonucleotide, PCR amplicon, plasmid DNA, viral DNA, bacterial DNA or any other DNA of known sequence or of sequence complementary to the target DNA or to a portion thereof, (3) *E. coli* RecA or a homologue thereof, as defined below.

As used herein and in the present claims (for the sake of brevity and clarity), the "RecA" or "SSB" is intended to include either the native or mutant *E. coli* RecA or SSB protein, or a "homologue" thereof as defined below. A "homologue" of RecA, SSB, etc., is a protein that has functional and, preferably, also structural similarity to its "reference" protein. One type of homologue is encoded by a homologous gene from another species of the same genus or even from other genera. As described below, these proteins, originally discovered in bacteria, have eukaryotic homologues in groups ranging from yeast to mammals. A functional homologue must possess the biochemical and biological activity of its reference protein, particularly the DNA binding selectivity or specificity so that it has the utility described herein. In view of this functional characterization, use of homologues of *E. coli* RecA or SSB proteins, including proteins not yet discovered, fall within the scope of the invention if these proteins have sequence similarity and the described DNA binding or biological activity or "improved" binding activity. Nonlimiting examples of improvements include a RecA homologue that binds to shorter DNA molecules or an SSB homologue with higher binding affinity for ss DNA.

"Homologues" is also intended to include those proteins which have been altered by mutagenesis or recombination that have been performed to improve the protein's desired function. These approaches are generally well described and well referenced below. Mutagenesis of a protein gene, conventional in the art, is generally accomplished in vivo by cloning the gene into bacterial vectors and duplicating it in cells under mutagenic conditions, e.g., in the presence of mutagenic nucleotide analogs and/or under conditions in which mismatch repair is deficient. Mutagenesis in vitro, also well-known in the art, generally employs error-prone PCR wherein the desired gene is amplified under conditions (nucleotide analogues, biased triphosphate pools, etc.) that favor misincorporation by the PCR polymerase. PCR products are then cloned into expression vectors and the resulting proteins examined for function in bacterial cells.

Recombination generally involves mixing homologous genes from different species, allowing them to recombine, frequently under mutagenic conditions, and selecting or screening for improved function of the proteins from the recombined genes. This recombination may be accomplished in vivo, most commonly in bacterial cells under mismatch repair-deficient conditions which allow recombination between diverged sequences and also increase the generation of mutations. Radman et al. have developed such methods of protein "evolution" (U.S. Pat. Nos. 5,912,119 and 5,965,415). In addition, Stemmer and colleagues have devised methods for both in vivo and in vitro recombination of diverged sequences to create "improved" proteins. Most involve PCR "shuffling" wherein two PCR amplicons of diverged sequences are digested and mixed together such that the fragments serve as both primer and template for additional PCR and, in so doing, combine different segments of the diverged genes, which is, in effect, genetic "recombination." Frequently, error prone PCR conditions are included to further stimulate generation of novel sequences. Resulting PCR products are cloned into expression vectors, and the resulting proteins are screened for improved function. See, for example, U.S. Pat. Nos. 5,512,463; 5,605,793; 5,81,238; 5,830,721; 5,837,458; 6,096,548; 6,117,679; 6,132,970; 6,165,793; 6,180,406; 6,251,674; 6,277,638; 6,287,861; 6,287,862; 6,291,242; 6,297,053; 6,303,344; 6,309,883; 6,319,713; 6,319,714; 6,323,030; 6,326,204; 6,335,160; 6,344,356.

As noted, homologues of the present invention generally share sequence similarity with their reference protein. To determine the % identity of two amino acid sequences (or of two nucleic acid sequences), the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred method of alignment, Cys residues are aligned. The length of a sequence being compared is at least 30%, preferably at least 40%, more preferably at least 50%, even more preferably at least 60%, and even more preferably at least 70%, 80%, or 90% of the length of the reference sequence (e.g., *E. coli* RecA). The amino acid residues (or nucleotides) at corresponding amino acid (or nucleotide) positions are then compared. When a position in the first sequence is occupied by the same amino acid residue (or nucleotide) as the corresponding position in the second sequence, then the molecules are identical at that position. As used herein amino acid or nucleic acid "identity" is also to be considered amino acid or nucleic acid "homology". The % identity between the two sequences is a function of the number of identical positions shared by the sequences, taking into account the number of gaps and the length of each gap which need to be introduced for optimal alignment. The comparison of sequences and determination of % identity between two sequences can be accomplished using mathematical algorithms, e.g., the Needleman and Wunsch (J. Mol. Biol. 48:444-453 (1970)) algorithm which has been incorporated into the GAP program (see below) using either a Blossom 62 matrix or a PAM250 matrix. A preferred program, "GAP" in the GCG software package, available at http://www.gcg.com, uses a NWSgapdna.CMP matrix and a gap weight of 40, 50, 60, 70, or 80 and a length weight of 1, 2, 3, 4, 5, or 6. In another approach, the % identity between two amino acid or nucleotide sequences is determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleic acid or protein sequence of a particular RecA or SSB protein can further be used as a "query sequence" to perform a search against public databases, for example, to identify other family members or related sequences. Such searches can be performed using the NBLAST and XBLAST programs (version 2.0) of Altschul et al. (1990) J. Mol. Biol. 215:403-410. To obtain gapped alignments for comparison purposes, Gapped BLAST can be utilized as described in Altschul et al. (1997) Nucl. Acids Res. 25:3389-3402. When using BLAST and Gapped BLAST, the default parameters of the respective programs can be used. See http://www.ncbi.nlm.nih.gov. For example, BLAST nucleotide searches can be performed with the NBLAST program, score=100, wordlength=12 to obtain nucleotide sequences homologous to a query RecA or SSB coding nucleic acid sequence. BLAST protein searches can be performed with the XBLAST program, preferably set at score=50, wordlength=3, to obtain amino acid sequences homologous to a query RecA or SSB protein molecule (e.g., wild-type sequence from E. coli).

Thus, a preferred homologue of an E. coli RecA protein or an E. coli SSB protein has, first and foremost, (a) the functional activity of native E. coli RecA or SSB and also preferably shares (b) a sequence similarity to the native E. coli protein, when determined as above, of at least about 20% (at the amino acid level), preferably at least about 40%, more preferably at least about 60%, even more preferably at least about 70%, even more preferably at least about 80%, and even more preferably at least about 90%.

At least 65 RecA genes from different bacteria have been cloned and sequenced (Sandier, S J et al., Nucl Acids Res 24:2125-2132 (1996); Roca, AI et al, Crit Rev Biochem Mol Biol 25:415-456 (1990); Eisen, J A, J. Mol. Evol. 41:1105-1123 (1995); and Lloyd, A T, et al., J. Mol. Evol. 37:399-407 (1993)). RecA homologues, known as RadA, have been identified in three archaean species (Sandler et al., supra; Seitz, E M, et al., Genes Dev. 12:1248-1253 (1998)). Eukaryotic homologues of RecA have been identified in every eukaryotic species examined; the prototype eukaryotic RecA homologue is the yeast Rad51 protein (Seitz et al., supra; Bianco, P R, et al., Frontiers Biosci. 3:570-603 (1998)). Therefore, any homologue of E. coli RecA which, like the E. coli protein, forms DNA filaments for initiation of genetic recombination as well as any functional form that has been mutated or evolved in vivo or in vitro is included within the scope of the present invention.

RecA functions in vitro, forming a three stranded structure involving oligonucleotides along sequence stretches as short as 15 nucleotides (Ferrin et al., 1991, supra). Combining the activities of RecA with genotype- or sequence-specific primer extension or oligonucleotide ligation creates a most powerful detection system for mutations/SNPs or specific sequences in which RecA-coated ssDNA catalyzes formation of a three strand (single D-loop) or four strand (double D-loop) structure without the need for prior denaturation of the test ds DNA.

In one preferred embodiment, the present system employs:
(1) RecA;
(2) specific probe oligonucleotides that contain 5' or internal adducts to allow immobilization; and
(3) detectably labeled nucleotide analogs for termination of primer extension.

Probe specificity derives from probe sequence. An oligonucleotide probe is designed to be complementary to the target DNA in the specific sequence of interest or adjacent to the site of mutation or SNP. For mutation or SNP detection, the 3' end of the oligonucleotide will be complementary to the nucleotide immediately 5' to the mutation or SNP site in the target DNA, such that the first nucleotide added to the oligonucleotide by DNA polymerase when the oligonucleotide is annealed to the target DNA will be complementary to the SNP or mutation allele.

Formation or stabilization of the D-loop formed by the RecA filaments and target DNA may be further enhanced by the addition of single strand binding (SSB) protein from E. coli or a homologue of SSB or by allowing double D-loop formation using an oligonucleotide complementary to the strand opposite that to which the oligonucleotide probe is complementary. When using an oligonucleotide in mutation or SNP detection to stabilize a single D-loop by forming a double D-loop, the stabilizing oligonucleotide must either terminate before the SNP or mutation site or must have a nucleotide at the site of the mutation or SNP that is not complementary to any allele of the mutation or SNP to prevent probe annealing and extension.

In the RecA/PE method, detection of mutations, SNPs and specific sequences is accomplished by detecting the covalent linkage (by DNA polymerase) of a genotype, allele or sequence specific labeled triphosphate or nucleotide terminator to the oligonucleotide probe molecule.

The DNA oligonucleotide probe may be of any length but is preferably a synthetic oligonucleotide, of about 30-60 bases in length and is specific for a genetic region that is being examined for the presence of a mutation or SNP or for its presence in a particular target DNA sample.

The target DNA may be of any length (up to an entire chromosome) and can be either genomic or plasmid DNA or a PCR amplicon.

The triphosphates or nucleotide terminators can be directly labeled with fluorophores or fluorescent labels, including, but not limited to, Fluorescein (and derivatives), 6-Fam, Hex, Tetramethylrhodamine, cyanine-5, CY-3, allophycocyanin, Lucifer yellow CF, Texas Red, Rhodamine, Tamra, Rox, Dabeyl.

RecA filament formation can be accomplished, for example, in a Tris-HCl or Tris-acetate buffer, (20-40 mM, pH 7.4-7.9) with MgCl2 or Mg acetate (1-4 mM), dithiothreitol (0.2-0.5 mM), and ATP or ATP[(-S] (0.3-1.5 mM). If ATP is used, an ATP regenerating system comprising phosphocreatine and creatine kinase may be included. RecA and oligonucleotide are generally added at a molar ratio of 0.1-3 (RecA to nucleotides). If the probe is double-stranded, it must first be denatured before RecA coating. Incubation is at room temperature or, preferably, 37EC, for 5-30 min. D-loop or triple strand structure formation involves adding RecA filaments to ds DNA and incubating, preferably at 37° C., for about 15 min-2 hrs. It is also possible to form RecA filaments and do homology searching in a single reaction vessel, i.e., to mix RecA with oligonucleotides and ds DNA at the same time. See, for example, Rigas et al., supra; Honigberg, S M, et al., Proc Natl Acad Sci USA 83:9586-9590 (1986); any of the Ferrin et al. publications (supra).

Primer extension can be accomplished by any primer dependent DNA polymerase (see Goelet, P et al, U.S. Pat. Nos. 5,888,819 and 6,004,744).

In another preferred embodiment the present system employs:
(1) RecA;
(2) specific oligonucleotides that contain adducts to allow immobilization (immobilization oligonucleotides); and
(3) specific detectably labeled oligonucleotides (reporter oligonucleotides) which are ligation partners for the immobilization oligonucleotides.

"Ligation partners" are pairs of oligonucleotides that are complementary to one strand of the target DNA and whose sequences are such that, when the partners are annealed to target DNA and the adjacent ends are perfectly base paired with the target DNA, they may be covalently linked by DNA ligase. For SNP and mutation detection, the ligation partners are selected so that the end of one (generally the reporter oligonucleotide) is complementary to one allele of the mutation or SNP such that ligation occurs only when the reporter oligonucleotide is annealed to target DNA of that allele. Thus, multiple, differently-labeled reporter oligonucleotides can be used in a single assay to allow complete genotyping of an SNP or mutation site. By using immobilization adducts, such as specific oligonucleotide sequences, that allow independent isolation of immobilization oligonucleotides, it is possible to obtain high levels of multiplexing.

When a single ligation partner set is used for a detection of a specific DNA sequence or mutation or SNP, i.e., all oligonucleotides complementary to one strand of the target DNA, single D-loops will be formed. Formation or stabilization of single D-loops formed by RecA filaments and target DNA may be further enhanced by the addition of single strand binding (SSB) protein from E. coli or a homologue of this protein (e.g., from another species) or by promoting double D-loop formation using an oligonucleotide complementary to the strand opposite that to which the probe is complementary. When using an oligonucleotide to stabilize a single D-loop by forming a double D-loop, the stabilizing oligonucleotide must have a nucleotide at the site of the mutation or SNP that is not complementary to any allele of the mutation or SNP to prevent probe annealing and ligation.

Figure 1:
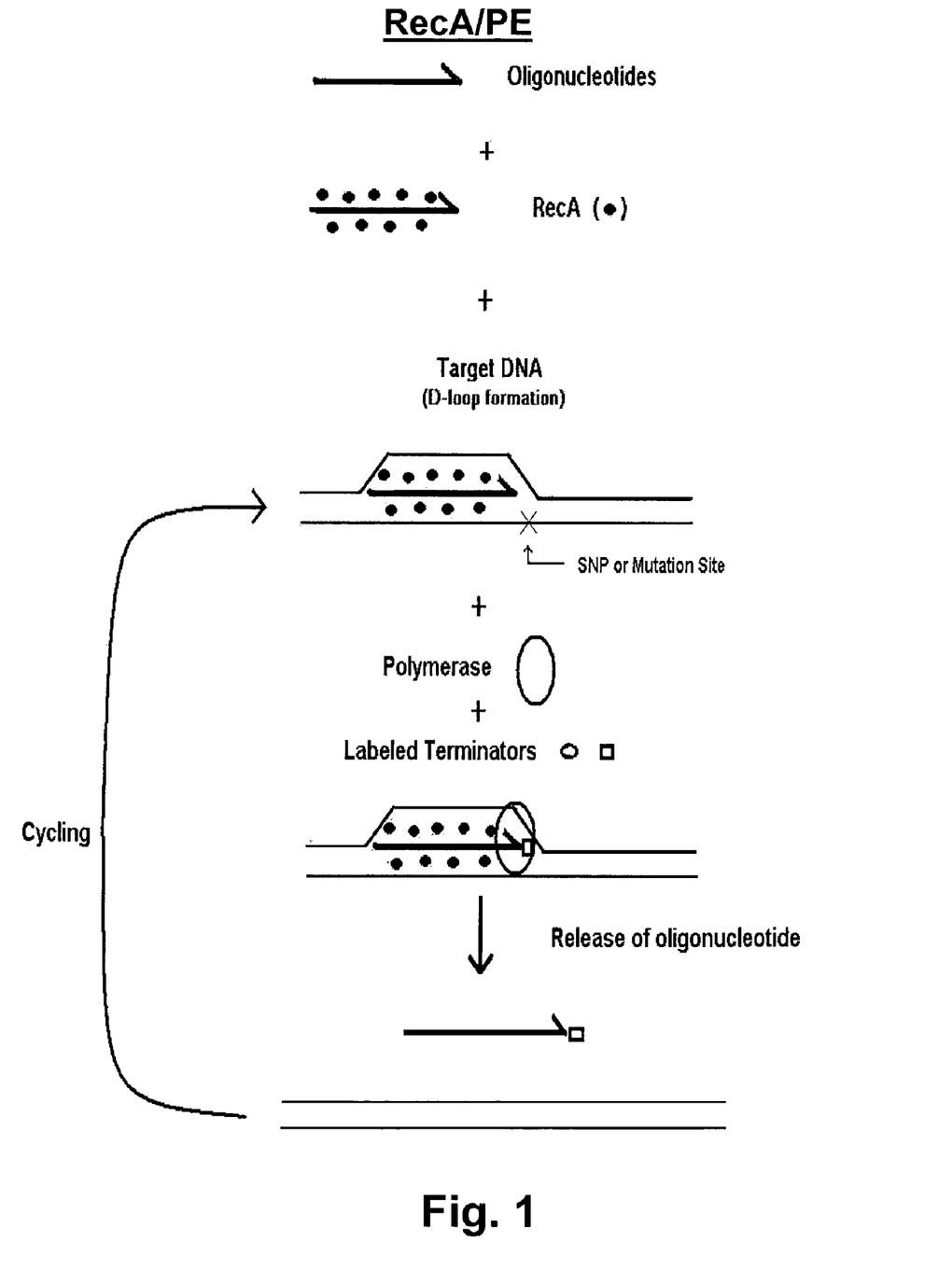
FIGS. 1-3 are schematic representations of RecA assisted mutation, SNP and specific sequence detection methodologies.
Figure 2:
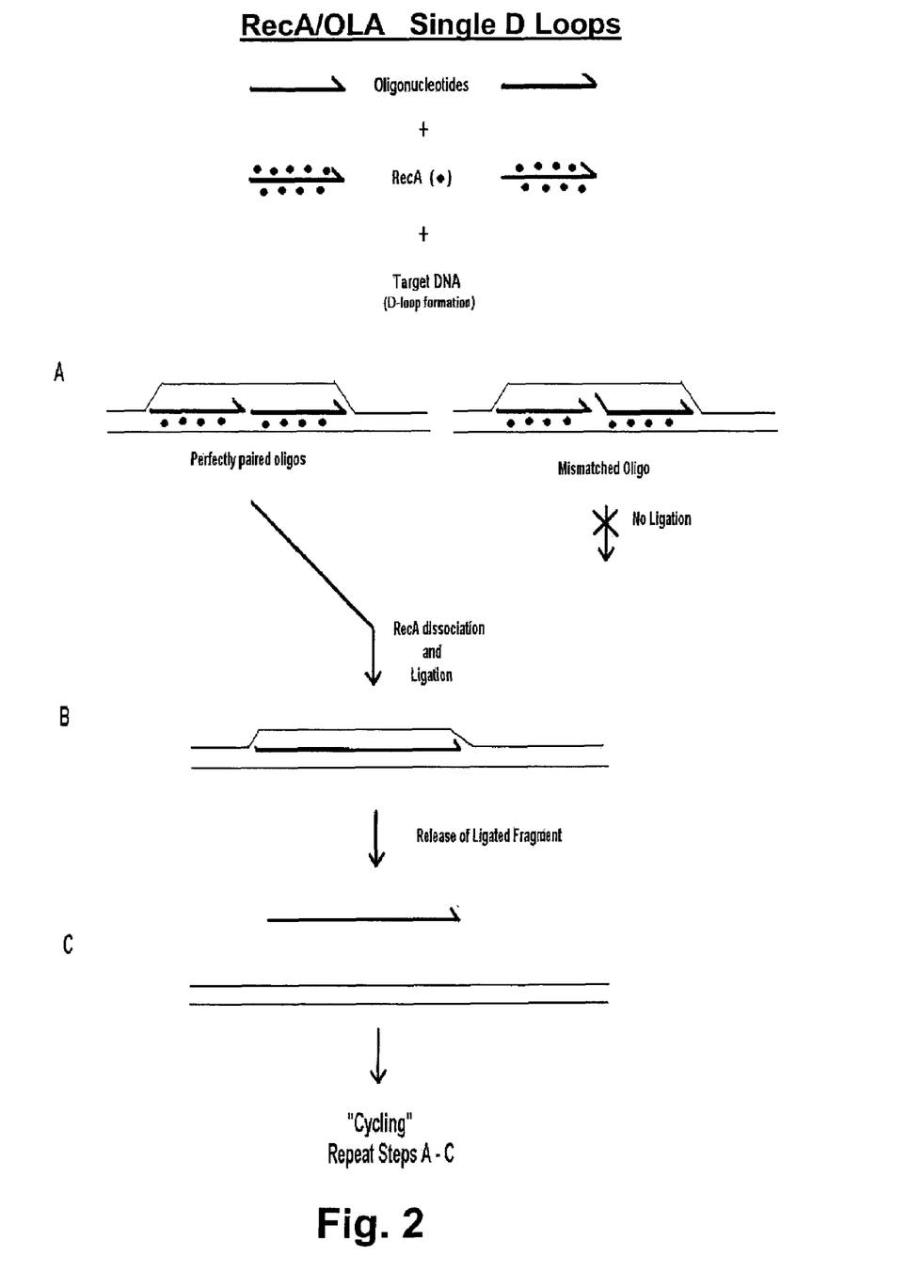
Figure 3:
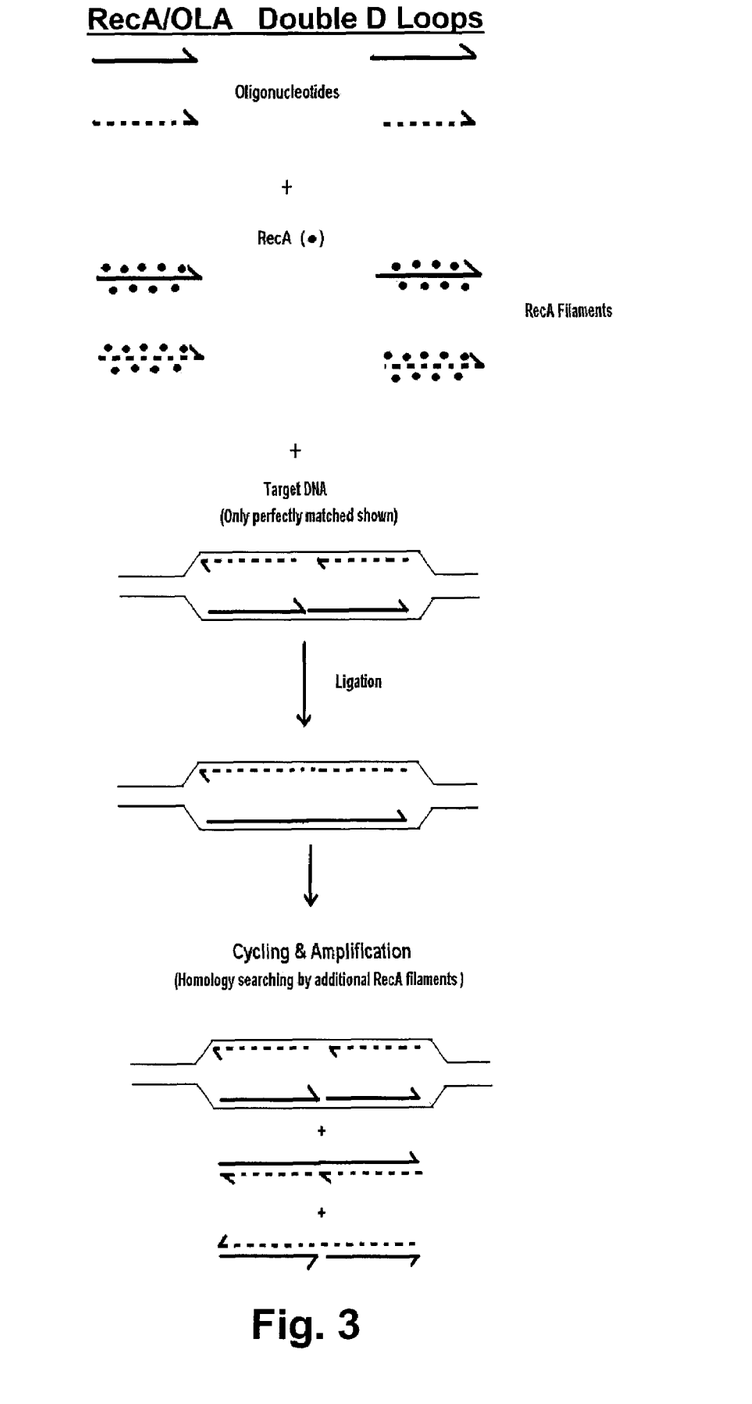

When ligation partners complementary to both strands of the target DNA are used, double D-loops will be formed. Stable double D-loops are perfect targets for additional RecA-mediated homology searching as are the ds oligonucleotides displaced from double D-loops by homology searching (see FIG. 3). Therefore, a RecA/OLA assay using double D-loop formation amplifies exponentially.

In the RecA/OLA method, detection of mutations, SNPs and specific sequences is accomplished by detecting the covalent linkage (by DNA ligation) of a pair of oligonucleotides, at least one of which is genotype-, allele- or sequence-specific.

Ligation may be accomplished by any DNA ligase, including, but not limited to, T4 ligase, E. coli ligase, Taq ligase, Rtth ligase and the like.

Ligation products may by detected simply by gel electrophoresis. The products will be of length equal to the sum of the two ligation partner oligonucleotides. Alternatively, one of the ligation partner oligonucleotides or plurality of oligonucleotides can contain an adduct, such as biotin or a specific oligonucleotide sequence (an "immobilization oligonucleotide"), to allow immobilization, and the other oligonucleotide or plurality of oligonucleotides may contain a detectable label ("reporter oligonucleotides"). Association of the detectable label with the immobilization oligonucleotide, under conditions where DNA probes have been separated from the target DNA or have been rendered single-stranded, is indicative of ligation. When multiple immobilization oligonucleotides or reporter oligonucleotides are employed, the precise nature of the ligation products, i.e., the precise nature of the association between immobilization adduct and reporter label is diagnostic of a particular sequence, allele or genotype in the target DNA.

The ligation partner oligonucleotides may be of any length but are preferably a synthetic oligonucleotide, of about 30-60 bases in length and are specific for a genetic region that is being detected in a ds DNA sample or is being examined for the presence of a mutation or SNP.

The target DNA may be of any length (up to an entire chromosome) and can be either genomic or plasmid DNA or a PCR amplicon.

The detectably-labeled oligonucleotides can be directly labeled with fluorophores or fluorescent labels, including, but not limited to, fluorescein (and derivatives), 6-Fam, Hex, tetramethylrhodamine, cyanine-5, CY-3, allophycocyanin, Lucifer yellow CF, Texas Red, rhodamine, Tamra, Rox, Dabcyl, etc. They may also be labeled with radioactive labels, digoxigenin, chemiluminescent labels or colorimetric labels.

RecA filament formation can be accomplished, for example, in a Tris-HCl or Tris-acetate buffer, (20-40 mM, pH 7.4-7.9) with $MgCl_2$ or Mg acetate (1-4 mM), dithiothreitol (0.2-0.5 mM), and ATP or ATP[γ-S] (0.3-1.5 mM). If ATP is used, an ATP regenerating system comprising phosphocreatine and creatine kinase may be included. RecA and oligonucleotide are generally added at a molar ratio of 0.1-3 (RecA:nucleotides). If the oligonucleotide is ds, it must first be denatured before RecA coating. Incubation is at room temperature or, preferably, 37° C., for 5-30 min. D-loop or triple strand structure formation involves adding RecA filaments to ds DNA and incubating, preferably at 37° C., for about 15 min-2 hrs. It is also possible to form RecA filaments and do homology searching in a single reaction vessel, i.e., to mix RecA with oligonucleotides and dsDNA at the same time. See, for example, Rigas et al., supra; Honigberg et al., supra; or any of the Ferrin et al. publications (supra).

When immobilization oligonucleotides are employed, immobilization may be to any suitable surface such as a microtiter plate, magnetic beads, beads suitable for detection via flow cytometry, etc. Detection may be via any the methods well known in the art including, but not limited to, photometric microplate readers and flow cytometry.

In one preferred embodiment of this invention, RecA is mixed with a synthetic oligonucleotide, of any length, but preferably of 30-60 bases in length, under conditions that allow formation of RecA filament. Filament formation may occur before or after addition of oligonucleotide to ds target DNA. Target DNA may be any dsDNA including, but not limited to, genomic DNA of any species, viral DNA, plasmid DNA, PCR amplicons, restriction fragments, or cloned DNA. The oligonucleotide is selected to be complementary to a specific region of the target DNA such that the 3' end of the oligonucleotide complementary to the base adjacent to the mutation or SNP to be detected.

Conditions are readily established, following formation of the RecA filament or following mixing of the RecA filament with target DNA, such that RecA filament can conduct a homology search on the target DNA. Provided complementary sequence exists in the target DNA, a triple stranded structure will be formed that will include a 3' end (of the oligonucleotide) suitable for extension by DNA polymerase. The DNA polymerase may be any polymerase and is not required to be thermostable. DNA polymerase is provided with one or more labeled DNA synthesis terminators. Most preferably, two different terminators will be provided to allow determination of all possible genotypes for any SNP or mutation involving a single base substitution. Preferred terminators are dideoxy or acyclo triphosphates and preferred labels are calorimetric, chemiluminescent or fluorescent labels.

Detection of incorporated labeled terminators is accomplished by separating the extended and, therefore, labeled oligonucleotides from unincorporated terminators. This is preferably accomplished by immobilizing the oligonucleotides, either by simply binding them to a solid support capable of binding DNA or by means of an adduct to the oligonucleotide, such as a 5' biotin or a short stretch of DNA at the 5' end of the primer which is not complementary to the target DNA, but which is complementary to an immobilized oligonucleotide. The complementary oligonucleotide method of immobilization allows multiplexing of the terminator reaction to examine multiple sites in a single target DNA sample and yet score them separately by having each specific oligonucleotide labeled with a different oligonucleotide "tail".

Detection of label may be accomplished by a variety of methods including, but not limited to, plate readers capable of detecting visible light or fluorescent signals, use of microchip readers and flow cytometry.

By allowing repeated formation of the triple stranded structure, preferably by performing homology searching in the presence of ATP, it is possible to have multiple oligonucleotides extended from each site in the target DNA.

In another preferred embodiment of this invention, RecA is mixed with two or more different synthetic oligonucleotides, each of any length, but preferably of 30-60 bases in length, under conditions that allow formation of RecA filaments. Filament formation may occur before or after addition of oligonucleotides to double-stranded target DNA. Target DNA may be any dsDNA including, but not limited to, genomic DNA of any species, viral DNA, plasmid DNA, PCR amplicons, restriction fragments, or cloned DNA. Oligonucleotide sequences are selected such that the oligonucleotides, when annealed to target DNA, abut at the site of the SNP or mutation in question. It is possible to ligate these oligonucleotides together only when the abutting ends are perfectly paired. Thus a mismatch at the end of one of the oligonucleotides will block ligation. By using differently labeled oligonucleotides such that there is a separate, distinctly labeled oligonucleotide complementary at its end nucleotide to only one of the alleles of the mutation or SNP to be detected, it is possible to fully genotype the site in question.

Labeling can be of any of the type mentioned above and will most preferably be restricted only to the allele specific oligonucleotides or set of oligonucleotides. Similarly, the oligonucleotides can be modified by any method to allow immobilization. Preferably, the oligonucleotide or set of oligonucleotides not labeled with the label intended for detection will be modified to allow immobilization, such that ligated molecules can easily be detected by any of the methods described above.

By allowing repeated formation of the triple stranded structure, preferably by performing homology searching in the presence of ATP, it is possible to have multiple ligations at each site in the target DNA.

Efficient RecA-catalyzed D-loop formation, primer extension or oligonucleotide ligation and flow cytometric signal detection, (5,000-20,000 sequences are sufficient for a genotype determination) allows as many as 1000 or more separate assays can be performed on a single ml of blood.

This technology is ideally suited to multiplexing wherein several sites in a single sample of genomic, plasmid or amplified DNA are interrogated simultaneously. In this application, specific probes are designed with adducts, most preferably oligonucleotide adducts that allow individual probes+target DNA (D-loop or triple strand structures) to be separately isolated from a mixture of many probes and target DNA. When oligonucleotides are used, isolation involves annealing the specific oligonucleotide adducts to immobilized oligonucleotides of complementary sequence.

A major advantage of the RecA assisted SNP, mutation and specific sequence detection technologies is that they can operate on genomic DNA without denaturation or amplification.

It is difficult to overstate the power of the RecA/PE and RecA/OLA methods. They are rapid, work with small samples and can readily be adapted to clinical applications for diagnostic genotyping and mutation/SNP detection. Further, the precision of RecA mediated homology searching allows the extremely accurate detection of infectious agents in samples with vast excesses of heterologous DNA. Perhaps the most important distinguishing advantage of the present inventions is their complete independence from DNA amplification (i.e., PCR).

Kits

The present invention is also directed to kit or reagent systems useful for practicing the methods described herein. Such kits will contain a reagent combination comprising the preferred elements required to conduct an assay according to the methods disclosed herein. The reagent system is presented in a commercially packaged form, as a composition or admixture where the compatibility of the reagents will allow, in a test device configuration, or more typically as a test kit, i.e., a packaged combination of one or more containers, devices, or the like holding the necessary reagents, and preferably including written instructions for the performance of assays. The kit of the present invention may be adapted for any configuration of assay and may include compositions for performing any of the various assay formats described herein.

Kits containing RecA, oligonucleotides and, where applicable, reagents for detection of fluorescent, chemiluminescent, radioactive or colorimetric signals, are within the scope of this invention. In one embodiment, a kit of this invention designed to allow detection of specific mutations and/or polymorphisms and/or in specific sequences of target DNA, includes one or more oligonucleotide probes specific for (a) a selected mutation and/or (b) a SNP, or (c) a specific region or regions of target DNA The probes may be labeled as described above. The kits also include a plurality of containers of appropriate buffers and reagents.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A method of detecting a single nucleotide polymorphism (SNP) in a double stranded target DNA molecule, comprising:
  (a) providing the following single stranded DNA oligonucleotide probes:
    (i) a first oligonucleotide probe complementary to a specific region of the target DNA, wherein, when the first probe is paired with said specific region of said target DNA, the 3' end base of said probe pairs with a base in the target DNA at or immediately adjacent to the site of SNP being detected;
    (ii) a second oligonucleotide probe complementary to said a specific region of the target DNA, wherein, when the second probe is paired with the specific region of said target DNA, the 5' end nucleotide of the probe pairs with a base in the target DNA at or immediately adjacent to the site of the SNP being detected; wherein the first and the second probes are complementary to adjacent, but non-overlapping, sequences in the target DNA, such that, when the probes are contemporaneously annealed to the target DNA, the 3' end of the first probe is paired with the base adjacent to the base to which the 5' end of said second probe is paired;
  (b) contacting the first and the second probes, with RecA protein to form RecA filaments;
  (c) contacting the RecA filaments with the target DNA, thereby forming a three stranded DNA D-loop structure in the target DNA, which D-loop structures comprise the probes and the two strands of the target DNA;
  (d) contacting the DNA D-loop structure with a DNA ligase, thereby joining the probes to form a ligation product;
  (e) detecting the presence of said ligation product, the presence of which is indicative of the presence of said SNP.

2. The method of claim 1 wherein said first or second probe is labeled with a fluorescent, radioactive, a chemiluminescent, an enzymatic, an antigenic or a colorimetric label.

3. The method of claim 1 wherein said first or second oligonucleotide probe further comprises an adduct that allows immobilization of the oligonucleotide probe before or after said ligation.

4. The method of claim 3 wherein the adduct is an oligonucleotide.

5. The method of claim 3 wherein the adduct is biotin or digoxigenin.

6. The method of claim 1, wherein the RecA protein is from *E. coli*.

7. The method of claim 1, wherein the detecting is by flow cytometry.

8. The method of claim 1, wherein the DNA D-loop structure formed in stabilized by the addition of a single stranded binding (SSB) protein.

9. The method of claim 1 wherein the target DNA molecule is selected from the group consisting of prokaryotic genomic DNA, eukaryotic genomic DNA, cDNA, viral DNA, plasmid DNA, and a DNA fragment amplified by PCR or by another amplification method.

10. The method of claim 1 wherein the oligonucleotide probe of (a) is selected from the groups consisting of: (a) a synthetic oligonucleotide; (b) a recombinant oligonucleotide; and (c) an oligonucleotide obtained by denaturing, and optionally cleaving, a double-stranded DNA molecule.

11. The method of claim 10, wherein the oligonucleotide probe has a length from 30 to 60 nucleotides.

* * * * *